United States Patent
Kim

(10) Patent No.: US 10,377,235 B2
(45) Date of Patent: Aug. 13, 2019

(54) VEHICLE SAFE STARTING DEVICE

(71) Applicant: LG Innotek Co., Ltd., Seoul (KR)

(72) Inventor: Dae Hwan Kim, Seoul (KR)

(73) Assignee: LG INNOTEK CO., LTD., Seoul (KR)

(*) Notice: Subject to any disclaimer, the term of this patent is extended or adjusted under 35 U.S.C. 154(b) by 26 days.

(21) Appl. No.: 15/553,903

(22) PCT Filed: Feb. 25, 2016

(86) PCT No.: PCT/KR2016/001856
§ 371 (c)(1),
(2) Date: Aug. 25, 2017

(87) PCT Pub. No.: WO2016/137246
PCT Pub. Date: Sep. 1, 2016

(65) Prior Publication Data
US 2018/0037113 A1 Feb. 8, 2018

(30) Foreign Application Priority Data
Feb. 26, 2015 (KR) .................. 10-2015-0027231

(51) Int. Cl.
*A61B 5/00* (2006.01)
*A61B 5/18* (2006.01)
(Continued)

(52) U.S. Cl.
CPC .......... *B60K 28/063* (2013.01); *A61B 5/1172* (2013.01); *A61B 5/1455* (2013.01);
(Continued)

(58) Field of Classification Search
None
See application file for complete search history.

(56) References Cited

U.S. PATENT DOCUMENTS 9,400,916 B1* 7/2016 Brownlee ............ A61B 5/1172
2002/0018584 A1* 2/2002 Johnson ............... A61B 5/1172
382/125
(Continued)

FOREIGN PATENT DOCUMENTS

JP 2008-290553 A 12/2008
JP 2008-302915 A 12/2008
KR 10-2013-0123014 A 11/2013

OTHER PUBLICATIONS

International Search Report in International Application No. PCT/KR2016/001856, filed Feb. 25, 2016.

*Primary Examiner* — Drew J Brown
(74) *Attorney, Agent, or Firm* — Saliwanchik, Lloyd & Eisenschenk

(57) ABSTRACT

The present invention relates to a vehicle safe starting device which controls the starting of a vehicle according to a driver's state. One embodiment analyzes blood alcohol concentration by projecting infrared rays into the driver's skin and receiving a reflected signal, and thereafter controls so that the vehicle is not stared if the blood alcohol concentration is larger than a reference value. Since a general breathalyzer using a driver's exhalation is not used, but infrared rays and a method of skin contact touch using a finger, etc. are used, it is possible to accurately measure the blood alcohol level without giving a driver inconvenience, and it is possible to preempt vehicle accidents by blocking driving in an inappropriate state.

13 Claims, 5 Drawing Sheets

(51) Int. Cl.
  *G07C 9/00* (2006.01)
  *B60K 28/00* (2006.01)
  *B60K 28/06* (2006.01)
  *B60K 35/00* (2006.01)
  *B60R 25/04* (2013.01)
  *B60R 25/25* (2013.01)
  *B60W 40/08* (2012.01)
  *B60W 50/08* (2012.01)
  *B60W 50/14* (2012.01)
  *A61B 5/1172* (2016.01)
  *A61B 5/1455* (2006.01)

(52) U.S. Cl.
  CPC .............. *A61B 5/18* (2013.01); *A61B 5/4845* (2013.01); *A61B 5/6893* (2013.01); *A61B 5/742* (2013.01); *B60K 28/06* (2013.01); *B60K 35/00* (2013.01); *B60R 25/04* (2013.01); *B60R 25/252* (2013.01); *B60W 40/08* (2013.01); *B60W 50/08* (2013.01); *B60W 50/14* (2013.01); *G07C 9/00087* (2013.01); *A61B 2562/0238* (2013.01); *B60K 2028/003* (2013.01); *B60K 2350/106* (2013.01); *B60K 2350/1028* (2013.01); *B60Y 2302/01* (2013.01)

(56) References Cited

U.S. PATENT DOCUMENTS

| | | | |
|---|---|---|---|
| 2005/0230175 A1 | 10/2005 | Brown et al. | |
| 2006/0239856 A1 | 10/2006 | Mobley et al. | |
| 2013/0070073 A1* | 3/2013 | Higuchi | A61B 5/1171 348/77 |
| 2017/0014058 A1* | 1/2017 | White | A61B 5/14552 |
| 2018/0047235 A1* | 2/2018 | Hyde | G07C 9/00563 |

* cited by examiner

VEHICLE SAFE STARTING DEVICE

CROSS-REFERENCE TO RELATED APPLICATIONS

This application is the U.S. national stage application of International Patent Application No. PCT/KR2016/001856, filed Feb. 25, 2016, which claims priority to Korean Application No. 10-2015-0027231, filed Feb. 26, 2015, the disclosures of each of which are incorporated herein by reference in their entirety.

TECHNICAL FIELD

The teachings in accordance with exemplary and non-limiting embodiments of this disclosure relate generally to a vehicle safe starting device, and more particularly to a vehicle safe starting device configured to prevent a safety accident caused by drunken driving by disallowing starting of a vehicle depending on a driver's state.

BACKGROUND ART

In general, a vehicle may be started by a driver using a vehicle key, and in addition, by various other methods of starting technologies such as touch panel, button method and remote controlled starting method. Meantime, technologies for preventing safety accidents caused by vehicle operation by a driver in an inadequate state for driving with regard to starting of a vehicle have been developed. For example, a Korean Registered Patent No.: 10-0816249 entitled as "apparatus for preventing drunken driving" has been disclosed in which an alcohol density of a driver is measured using breath of a driver and a rotation of a key is allowed according to the measured density of alcohol to prevent the drunken driving.

However, the conventional technologies suffer from disadvantages because the breath of a driver is used to make measurement inaccurate, it provides a discomfort in the course of a driver inputting a breath of the driver and it is difficult to apply due to changed structure of key box.

DETAILED DESCRIPTION OF THE INVENTION

Technical Subject

The present disclosure is provided to solve the aforementioned disadvantages of the prior art, and it is an object of the present disclosure is to provide a vehicle safe starting device configured to prevent a driving of an inadequate state such as a drunken driving by allowing starting of a vehicle depending on a driver's state and to realize measurement of the driver's state in a more accurate and comfortable manner.

Technical Solution

In order to solve the technical subject, and in one general aspect of the present disclosure, there is provided a vehicle safe starting device, comprising:
a touch part physically contacting skin of a man;
an optical sensor part projecting an electromagnetic wave of a predetermined frequency region to the skin of a man contacted by the touch part, and receiving a reflective signal of the projected electromagnetic wave; and
an analysis part analyzing the reflective signal and outputting a start control signal as a result of the analysis.

Preferably, but not necessarily, the touch part may be formed with a transparent tempered glass material configured to contact the skin of a man.

Preferably, but not necessarily, the optical sensor part may project an infrared ray using the electromagnetic wave.

Preferably, but not necessarily, the analysis part may calculate a blood alcohol density by analyzing the reflective signal and output the start control signal in response to a comparative result between the blood alcohol density and a reference value.

Preferably, but not necessarily, the device further comprises a display part visually displaying information analyzed by the analysis part.

Preferably, but not necessarily, the frequency region may be 9.6 um.

Preferably, but not necessarily, the device further comprises: a fingerprint recognition part recognizing a fingerprint of a driver; and
a driver certification part ascertaining a registered driver by comparing with a pre-registered fingerprint while receiving a fingerprint signal from the fingerprint recognition part.

Preferably, but not necessarily, the fingerprint recognition part may obtain a fingerprint of a driver, and the optical sensor part may obtain information on alcohol from other parts than a part where the fingerprint was obtained in the finger.

Preferably, but not necessarily, the fingerprint recognition part may obtain information from a first joint of the finger, and the optical sensor part may obtain information from a second joint of a finger.

Preferably, but not necessarily, the fingerprint recognition part and the optical sensor part may respectively obtain information by being overlapped for at least a predetermined time.

Advantageous Effects of the Disclosure

The advantageous effect according to the present disclosure is that a vehicle is not started when a driver's state is inadequate for driving to thereby prevent a safety accident, and to fundamentally prevent a drunken driving.

In case of measurement of alcohol density, no discomfort is provided to a driver because of using a touch method of contacting a finger and using an infrared ray, instead of using a conventional breathalyzer with breath of a driver, whereby an accurate alcohol measurement is enabled and a high class atmosphere of smart car environment can be felt.

Furthermore, concomitant with display of driver's analyzed state and use of combination with various bio sensors necessary for individual driver, demands requiring various functions can be satisfied as the market of ADAS (Advanced Driver Assistance System) grows.

BEST MODE

Hereinafter, a vehicle safe starting device according to an exemplary embodiment of the present disclosure will be described in detail with reference to the accompany drawings.

Figure 1:
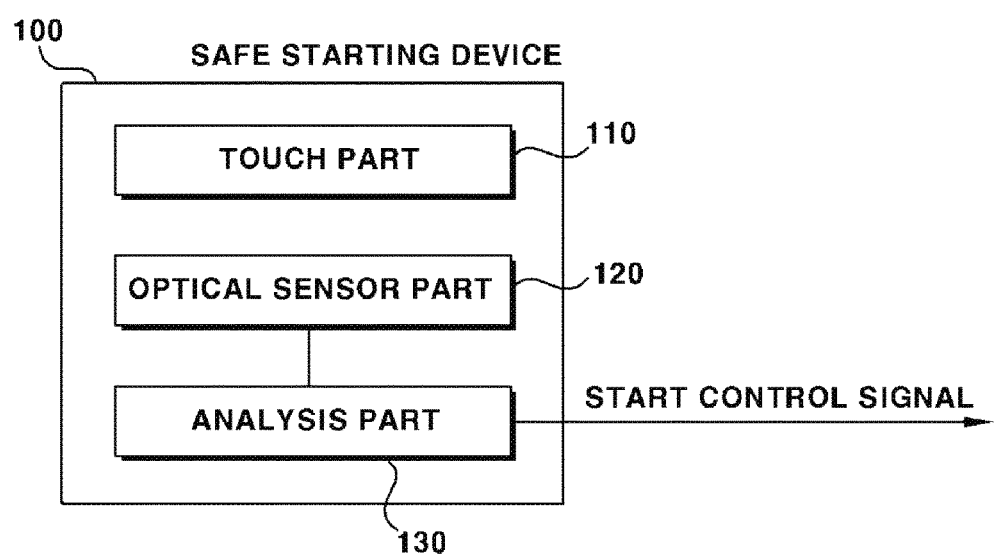
FIG. 1 is a schematic diagram illustrating a vehicle safe starting device according to an exemplary embodiment of the present disclosure.

Referring to FIG. 1, a vehicle safe starting device (100, hereinafter referred to as "safe starting device") according to an exemplary embodiment of the present disclosure may include a touch part (110), an optical sensor part (120) and an analysis part (130), and perform a function of controlling the start of a vehicle.

The touch part (110) may be physically touched to a skin of a man where the skin touched by the touch part (110) may be variably set. For example, a finger part of a driver who wishes to start a vehicle may be made to be touched by the touch part (110). The touch part (110) physically touches a skin of a man and therefore is allowed to be exposed to contact the skin of the driver, and may be disposed at any arbitrary place inside a vehicle to allow the driver to comfortably touch the skin such as a finger of the driver.

Furthermore, the touch part (110) must allow the electromagnetic wave to pass therethrough easily, and for example, the touch part (110) may be formed with a transparent tempered glass material.

The optical sensor part (120) may project an electromagnetic wave of a predetermined frequency region to a skin of a man contacted by the touch part (110), and perform a function of receiving a reflective signal therefrom. The electromagnetic wave is used to measure a driver's state, and electromagnetic wave of an arbitrary frequency region may be used as long as safety is guaranteed with physical properties capable of measuring the driver's state.

An example of a driver's state determining whether a driver is adequate to drive a vehicle may be blood alcohol density and an infrared ray may be used as an electromagnetic wave usable for measuring blood alcohol density. For example, alcohol density may be measured by using a PTC (Photothermal Radiometry) method. That is, when a pulse beam is projected to a driver, a thermal wave is generated. When a wave in a pre-stored normal state and a wave generated by being projected to a driver are compared, a blood alcohol density may be calculated. At this time, the pulse beam may be projected to a physical part of a driver, for example, to a finger part of a driver. A light source of wavelength may be used that has a greater absorption rate of alcohol in the pulse beam. Preferably, a light source having a wavelength of 9.6 um may be used.

The analysis part (130) may analyze a reflective signal received through the optical sensor part (120), and determine whether a driver is in a state of driving a vehicle or a driver is in an inadequate state of driving a vehicle, and output a start control signal as a result of the determination. An electromagnetic wave projected from the optical sensor part (120) and an electromagnetic wave received from reflection may generate a difference depending on physical properties of relevant electromagnetic wave or state inside a skin of a man projected with relevant electromagnetic wave, such that the analysis part (130) can determine a state of a driver using various determination methods depending on the differences.

Albeit not being illustrated, the safe starting device (100) may further comprise a fingerprint recognition part and a driver certification part. The fingerprint recognition part may be formed at a partial area of the touch part (110) or may be formed separately from the touch part (110). In case the fingerprint recognition part is separately formed, a body part obtaining information on the fingerprint and a body part obtaining information on alcohol may be different.

For example, the fingerprint recognition part may obtain fingerprint information from a finger of a driver, and the optical sensor part may obtain information on alcohol from other finger except for the part obtained with the fingerprint information. For example, fingerprint information from a first finger joint formed with a fingerprint can be extracted and information on alcohol from the second joint of a finger may be obtained.

Furthermore, the fingerprint recognition part and the optical sensor part may simultaneously obtain information or may individually obtain information by being overlapped for at least a predetermined time, and the fingerprint recognition and the alcohol measurement may allow information to be simultaneously obtained or obtained for a predetermined time by being overlapped, whereby reliable information as alcohol density information registered on a vehicle can be provided.

The driver certification part may receive a fingerprint signal from the fingerprint recognition part to compare same with pre-stored fingerprint information of a vehicle user and check if the information is the one of registered driver.

A driver is first ascertained through the abovementioned processes and next processes are proceeded to further reinforce the safety. For example, when a vehicle owner drives a vehicle under the influence of alcohol, and when there is no certification process of the vehicle owner through the fingerprint recognition, a start control signal may be outputted by measuring a blood alcohol density of other person than the driver. Thus, when a driver certification part is disposed as in the exemplary embodiment of the present disclosure, measurement of other person's blood alcohol density can be prevented.

Figure 2:
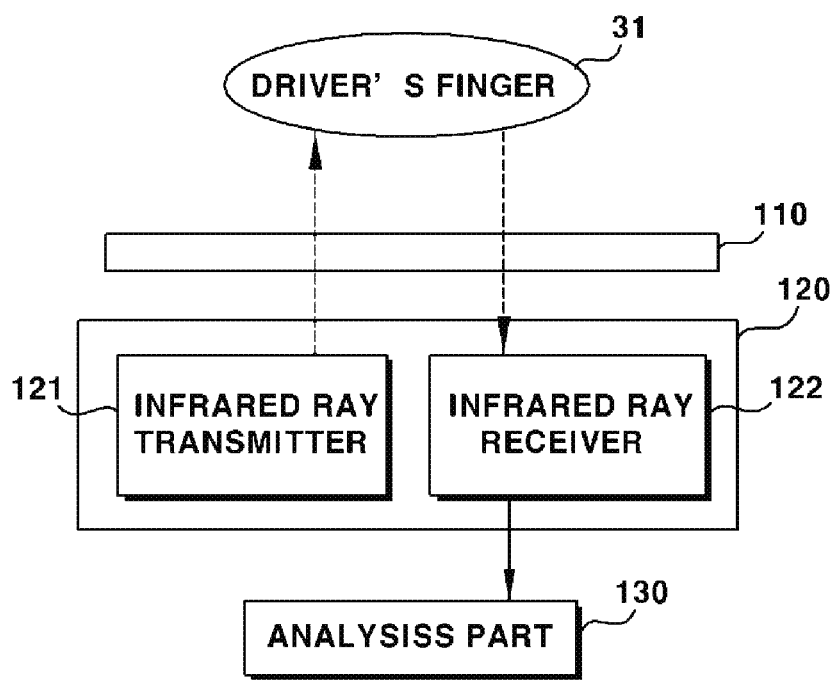
FIG. 2 is a schematic diagram illustrating a vehicle safe starting device using an infrared ray according to an exemplary embodiment of the present disclosure.

Referring to FIG. 2, the optical sensor part (120) may be formed by including an infrared ray transmitter (121) such as an infrared ray LED (Light Emitting Diode) and an infrared ray receiver (122) configured to detect an infrared ray. The infrared ray projected through the infrared ray transmitter (121) may pass the transparently materialed touch part (110) to be incident on a driver finger (31), where the infrared ray is absorbed in response to inner characteristic of a driver finger and reflected to be detected by the infrared ray receiver (122). Then, the analysis part (130) may determine a driver's state by analyzing the received infrared ray.

As a detailed example, the analysis part (130) may calculate a blood alcohol density of a driver by analyzing a reflective signal. That is, when an infrared ray is incident on a skin of a man, an absorption rate is changed depending on an amount of alcohol component existent in the blood, such that the blood alcohol density of a driver can be accurately measured when the reflective signal is analyzed. Furthermore, a start control signal can be outputted in response to the analyzed blood alcohol density.

Figure 3A:
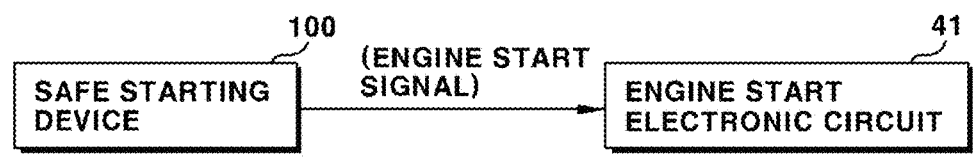
FIGS. 3a and 3b are schematic views illustrating a vehicle safe starting device according to an exemplary embodiment of the present disclosure.
Figure 3B:
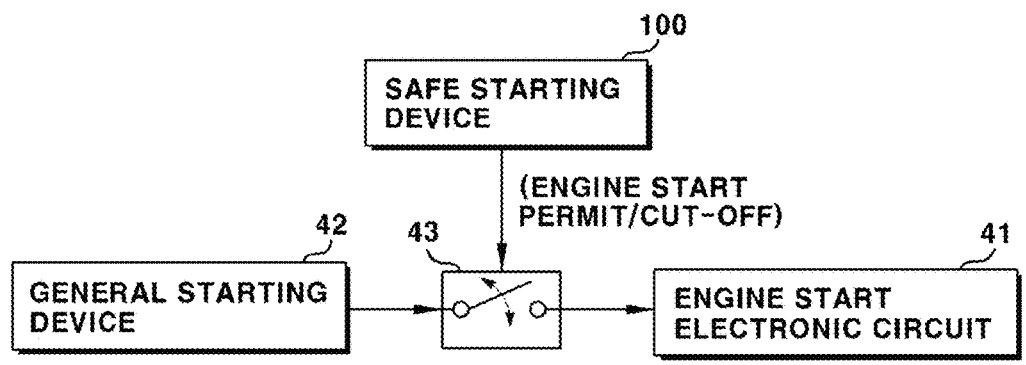

FIGS. 3a and 3b are schematic views illustrating a vehicle safe starting device (100) according to an exemplary embodiment of the present disclosure, where the safe starting device (100) may be applied in various methods.

Referring to FIG. 3a, the safe starting device (100) may transmit an engine start signal to an electronic circuit (41) taking charge of starting an engine. Here, the terms of engine start signal is a signal transmitted to the electronic circuit (41) when a vehicle is started, where the safe starting device (100) itself can independently perform a function of a vehicle starting device.

Furthermore, as illustrated in FIG. 3b, the safe starting device (100) can perform a function of an auxiliary device capable of enabling an engine start. The start control signal outputted from the safe starting device (100) may control a switching element (43) to perform a function of transmitting an engine start signal inputted through a general start device (42) to the electronic circuit (41) or cutting off the engine start signal. Here, the terms of general start device (42) means a device generally used for starting a vehicle with a key, a touch method or a button method.

Thus, a driver must start a vehicle through the general start device such as a key, a touch method or a button method after entering into a startable state by first checking a drivable state through the safe starting device (100).

Figure 4:
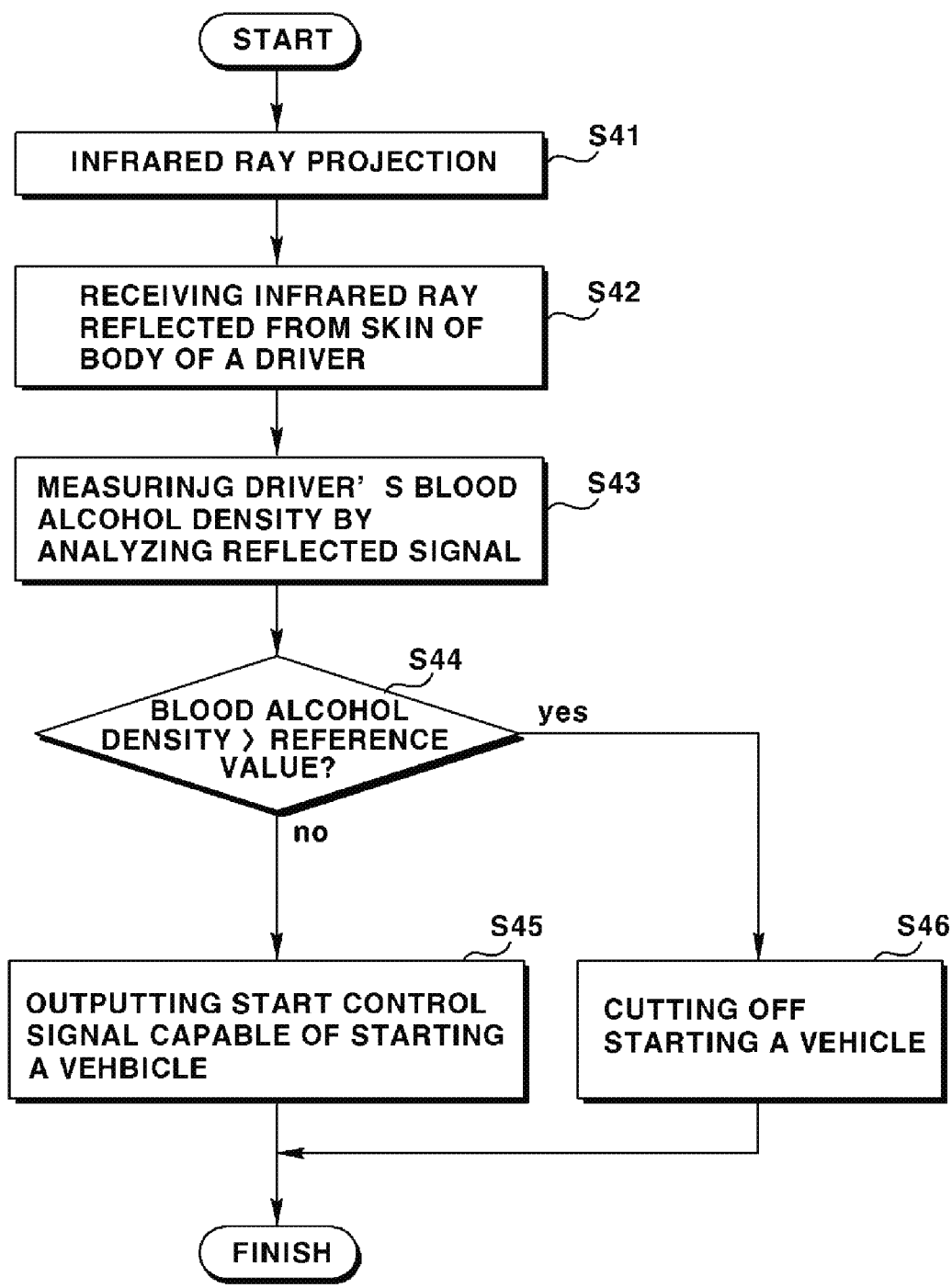
FIG. 4 is an operation process of a vehicle safe starting device according to an exemplary embodiment of the present disclosure.

FIG. 4 is an operation process of a vehicle safe starting device (100) according to an exemplary embodiment of the present disclosure.

When an infrared ray is irradiated through the infrared ray transmitter (121) (S41), the infrared ray is reflected by being incident on the skin of a driver to be received through the infrared ray receiver (122) (S42), where the analysis part (130) may determine the blood alcohol density of the driver by analyzing the infrared ray (S43). As a result of the determination, if the blood alcohol density of the driver is less than a reference value (S44), an engine control signal capable of starting a vehicle is outputted to realize the engine starting (S45), and if the blood alcohol density of the driver is not less than a reference value, the start of an engine is cut off to prevent the driving (S44, S46).

Figure 5:
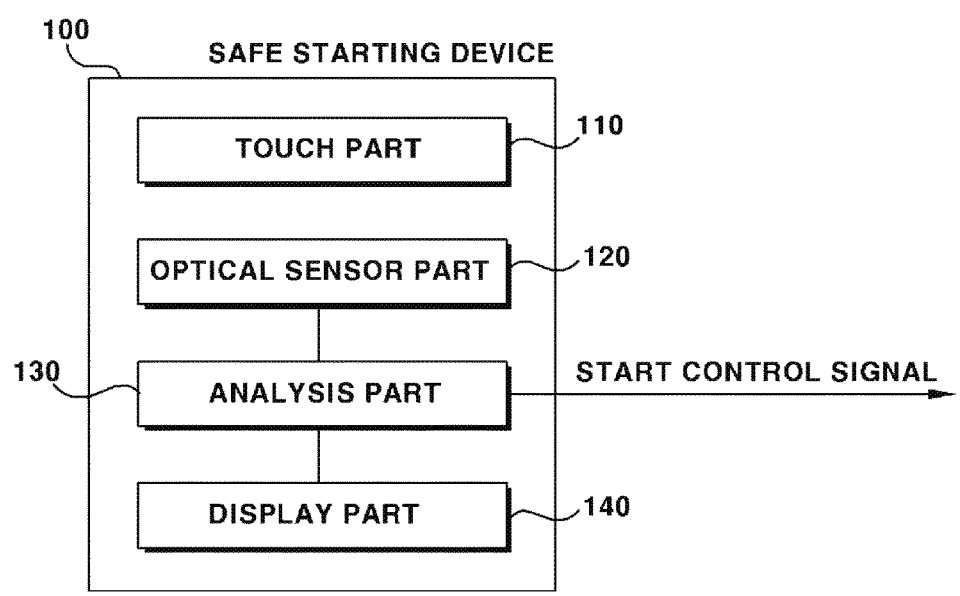
FIG. 5 is a schematic view illustrating a vehicle safe starting device according to another exemplary embodiment of the present disclosure.

Referring to FIG. 5, the vehicle safe starting device (100) may be configured by being further comprised of a display part (140) that visually displays the information analyzed by the analysis part (130). At this time, the analysis part (130) may output the start control signal and other detailed analyzed information as well, where the display part (140) may receive the analyzed information from the analysis part (130) to display the information on a screen in various types.

For example, the display part (140) may display a blood alcohol density value of a driver. Particularly, glucose and alcohol have similar absorption rate relative to the infrared ray, such that a driver suffering from diabetes can learn his or her own blood sugar information whenever starting a vehicle. Furthermore, the vehicle safe starting device (100) may be so configured as to interact with various types of bio sensors capable of measuring a driver's state, and in this case, various pieces of information related to the driver's state can be displayed on the display part (140).

Although the abovementioned embodiments according to the present disclosure have been described in detail with reference to the above specific examples, the embodiments are, however, intended to be illustrative only, and thereby do not limit the scope of protection of the present disclosure. Thereby, it should be appreciated by the skilled in the art that changes, modifications and amendments to the above examples may be made without deviating from the scope of protection of the disclosure.

INDUSTRIAL APPLICABILITY

The present disclosure may be applied to a vehicle.

The invention claimed is:

1. A vehicle safe starting device, comprising:
   a touch part for physically contacting skin of a human;
   an optical sensor part comprising a transmitter that projects an electromagnetic wave of a predetermined frequency region to the skin of a human contacted by the touch part, and a receiver that receives a signal of the projected electromagnetic wave reflected by the skin of the human; and
   an analysis part that analyzes the reflective signal and outputs a start control signal as a result of the analysis;
   wherein the transmitter and the receiver are disposed in a horizontal direction that is in parallel to the touch part.

2. The vehicle safe starting device of claim 1, wherein the touch part is formed with a transparent tempered glass material configured to contact the skin of a human.

3. The vehicle safe starting device of claim 1, wherein the optical sensor part projects an infrared ray using the electromagnetic wave.

4. The vehicle safe starting device of claim 1, wherein the analysis part calculates a blood alcohol density by analyzing the reflective signal and outputs the start control signal in response to a comparative result between the blood alcohol density and a reference value.

5. The vehicle safe starting device of claim 1, comprising a display part that visually displays information analyzed by the analysis part.

6. The vehicle safe starting device of claim 1, wherein the frequency region is 9.6 um.

7. The vehicle safe starting device of claim 1, further comprising:
   a fingerprint recognition part for recognizing a fingerprint of a driver; and
   a driver certification part that ascertains a registered driver by comparing with a pre-registered fingerprint while receiving a fingerprint signal from the fingerprint recognition part.

8. The vehicle safe starting device of claim 7, wherein the fingerprint recognition part obtains a fingerprint of a driver, and the optical sensor part obtains information on alcohol from other parts than a part where the fingerprint was obtained on the finger.

9. The vehicle safe starting device of claim 7, wherein the fingerprint recognition part obtains information from a first joint of the finger, and the optical sensor part obtains information from a second joint of a finger.

10. The vehicle safe starting device of claim 7, wherein the fingerprint recognition part and the optical sensor part respectively obtain information by being overlapped for at least a predetermined time.

11. The vehicle safe starting device of claim 1, wherein the vehicle safe starting device transmits an engine start signal to an electronic circuit taking charge of starting an engine, and
   wherein the engine start signal is a signal transmitted to the electronic circuit when a vehicle is started.

12. The vehicle safe starting device of claim 11, wherein the safe starting device outputs a start control signal and the start control signal controls a switching element to perform a function of transmitting the engine start signal inputted through a general start device to the electronic circuit or of cutting off the engine start signal, and
   wherein the general start device means a device generally used for starting a vehicle with a key, a touch method, or a button method.

13. The vehicle safe starting device of claim 1, wherein a direction of the electromagnetic wave projected from the transmitter is in parallel to a direction of the reflected signal received by the receiver.

* * * * *